US008227612B2

(12) United States Patent
Cai et al.

(10) Patent No.: US 8,227,612 B2
(45) Date of Patent: Jul. 24, 2012

(54) QUINOLINE COMPOUND AND PHARMACEUTICAL COMPOSITION, PREPARATION METHOD AND USES THEREOF

(75) Inventors: Zhengyan Cai, Shanghai (CN); Weicheng Zhou, Shanghai (CN); Qun Hao, Shanghai (CN); Zhenhua Shi, Shanghai (CN); Yuchen Sheng, Shanghai (CN); Mingyu Shi, Shanghai (CN); Qingning Liang, Shanghai (CN)

(73) Assignee: Shanghai Institute of Pharmaceutical Industry, Shanghai (CN)

( * ) Notice: Subject to any disclaimer, the term of this patent is extended or adjusted under 35 U.S.C. 154(b) by 8 days.

(21) Appl. No.: 12/935,212

(22) PCT Filed: Apr. 29, 2009

(86) PCT No.: PCT/CN2009/071573
§ 371 (c)(1),
(2), (4) Date: Sep. 28, 2010

(87) PCT Pub. No.: WO2009/132593
PCT Pub. Date: Nov. 5, 2009

(65) Prior Publication Data
US 2011/0021561 A1    Jan. 27, 2011

(30) Foreign Application Priority Data

Apr. 30, 2008   (CN) .......................... 2008 1 0036930

(51) Int. Cl.
C07D 215/22    (2006.01)
C07D 215/233   (2006.01)
C07D 215/36    (2006.01)

(52) U.S. Cl. ....................................... 546/153; 546/155

(58) Field of Classification Search ........................ None
See application file for complete search history.

(56) References Cited

U.S. PATENT DOCUMENTS

2005/0227947 A1* 10/2005 Chen et al. ...................... 514/79

FOREIGN PATENT DOCUMENTS

| CN | 101210011 A | 7/2008 |
| CN | 101220021 A | 7/2008 |
| WO | WO 2008/077305 A1 | 7/2008 |
| WO | WO 2008/083551 A1 | 7/2008 |

OTHER PUBLICATIONS

Vippagunta et al., "Crystalline Solids", 48 Adv. Drug Delivery Rev. 3-26 (2001).*
Philip J. Kocienski, Protecting Groups, p. 120, (Thieme, 3rd Ed., 2005) (1994).*
Berge et al., Pharmaceutical Salts, 66(1) J. Pharma. Sci. 1-19 (1977).*
Cai et al., "Progresses in researches of HMG CoA reductase inhibitors", Chinese Journal of New Drugs, vol. 15, No. 22, pp. 1907-1912, 2006.
Cai et al., "Synthesis and HMG CoA reductase inhibition of 4-thiophenyl quinolines as potential hypocholesterolemic agents", Bioorganic & Medicinal Chemistry, vol. 15, pp. 7809-7829, Aug. 28, 2007.
Cai et al., "Synthesis of Pitavastatin Calcium", Chinese Journal of Pharmaceuticals, vol. 38, No. 3, pp. 177-180, 2007.
International Search report dated Jul. 30, 2009 in Application No. PCT/CN2009/071573.

* cited by examiner

*Primary Examiner* — Janet Andres
*Assistant Examiner* — Timothy R Rozof
(74) *Attorney, Agent, or Firm* — Birch Stewart Kolasch & Birch, LLP

(57) ABSTRACT

The present invention discloses a quinoline compound represented by the formula A or pharmaceutically acceptable solvate, optical isomer or polymorph thereof,

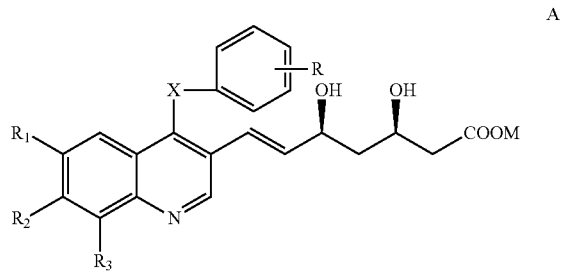

wherein X is S or O; M is H, $Na^+$, $NH4^+$ or $Ca^{2+}$; each of $R_1$, $R_2$ and $R_3$ is independently H, halogen, the group represented by formula D or formula E; R is H, halogen, C1~C4 alkyl or C1~C4 alkoxy.

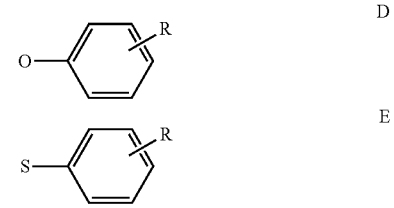

The present invention also discloses its pharmaceutical composition and the preparation method thereof and application in manufacturing a medicament for inhibiting HMG-CoA reductase or for the treatment and prophylaxis of the diseases which can be treated effectively by inhibiting HMG-CoA reductase. The quinloline compound and pharmaceutical composition thereof of the present invention have an excellent lipid reduction effect in vivo and can be applied for treatment of a hyperlipidemia-related disease.

12 Claims, No Drawings

QUINOLINE COMPOUND AND PHARMACEUTICAL COMPOSITION, PREPARATION METHOD AND USES THEREOF

FIELD OF THE TECHNOLOGY

The present invention pertains to the field of synthesis technology in medicinal chemistry. More particularly, this invention is related to a novel quinoline compound and a pharmaceutical composition comprising the same, the preparation methods and applications in pharmaceutical field.

BACKGROUND

Antihypercholesterolemic agents have evolved rapidly since hypercholesterolemia was well recognized as a primary risk factor in atherosclerotic and cardiovascular diseases.

A class of drugs, such as 3-hydroxy-3-methylglutaryl-CoA reductase (HMG-CoA reductase) inhibitors, as called statins, is currently potent antihypercholesterolemic agents. (Cai Zhengyang, Zhou Weicheng. Progresses in researches of HMG-CoA reductase inhibitors, Chinese Journal of New Drugs, 2006, 15 (22): 1907-1911).

The launched drugs, lovastatin, simvastatin, pravastatin, fluvastatin, atorvastatin, rosuvastatin, and pitavastatin are currently available antihypercholesterolemic agents.

In the prior arts, the structure of totally synthetic statins is composed of a framework such as quinoline, indole, pyrrole, pyrimidime and a side chain.

Systematical QSAR studies on quinoline statin compounds, such as pitavastatin, show that the introduction of the side chains to position 3 in quinoline exhibited a good activity in inhibiting HMG-CoA reductase. The introduction of chloro, methyl or methoxy etc. to the 6-, 7- or 8-position of the quinoline nucleus may increase the inhibitory potency. (Cai Z-Y, Zhou W-C. Progresses in researches of HMG-CoA reductase inhibitors, Chinese Journal of New Drugs, 2006, 15 (22): 1907-1911).

The Chinese patent applications, No. 200610148118.4 and 200710036427.7, disclosed the quinoline derivatives in which a thiophenyl and a phenoxy was introduced to position 4 respectively, and the side chains have a lactone structure. Both of said quinoline derivatives demonstrate a good activity in inhibiting HMG-CoA reductase in vitro experiments. However, as far as human requirement is concerned, there is a need to develop new potent antihypercholesterolemic drugs.

DETAILED DESCRIPTION OF THE INVENTION

Since the existing HMG-CoA reductase inhibitors having the side chains of lactone can not provide sufficient effects on lowering blood lipid to meet demands of human beings, an object of the present invention is to provide a new potent quinoline compound for lowering blood lipid, and a pharmaceutical composition, the preparation method and applications thereof.

Upon investigation and research, the inventors have found it has already been reported that the statin compound with an open 3,5-dihydroxy pentanoic acid (or salt) in the side chain had better effects on lowering blood lipid than a compound having a side chain of lactone structure (J Med Chem, 1985, Vol. 28, P. 347-358), and that the launched statins have a chemical structure of 3,5-dihydroxy heptenoic acid salt. Therefore, based on the above reports, the inventors of present invention have done plenty of research and found that a carboxylic acid (or salt) of quinoline derivatives can be prepared by ring-opening of the lactone in the side chain of quinoline derivatives. It has been proved that such a carboxylic acid (or salt) provides an excellent activity in lowering blood lipid.

Therefore, the first object of present invention is to provide a quinoline compound represented by Formula A or the pharmaceutically acceptable solvate, optical isomer or polymorph thereof,

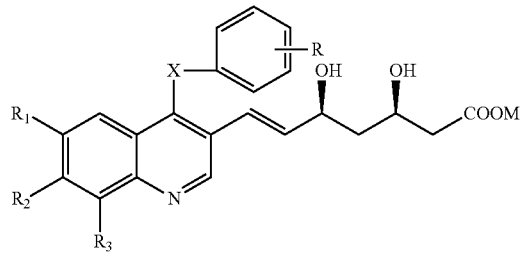

A

Wherein
X is S or O; M is H, $Na^+$, $NH_4^+$ or $Ca^{2+}$; each of $R_1$, $R_2$ and $R_3$ is independently H, halogen, a substituent represented by Formula D or Formula E;

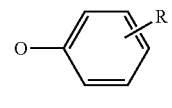

D

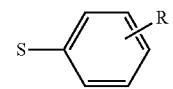

E

Wherein
R is H, halogen, C1~4 alkyl or C1~4 alkoxy.

According to the present invention, said halogen is F, Cl, Br, or I, and more preferably is F or Cl. Said $C_1$-$C_4$ alkyl is preferably methyl, ethyl, n-propyl, isopropyl, cyclopropyl or n-butyl. Said $C_1$-$C_4$ alkoxy is preferably methoxy, ethoxy, n-propoxy, isopropoxy, or n-butoxy.

According to the present invention, the quinoline compound is preferably:
(3R,5S)-7-[6,7,8-trifluoro-4-(4-fluorothiophenyl)quinoline-3-yl]-3,5-dihydroxy-6(E)-heptenoic acid sodium salt,
(3R,5S)-7-[6-fluoro-4,7-di-(thiophenyl)quinoline-3-yl]-3,5-dihydroxy-6(E)-heptenoic acid ammonium salt,
(3R,5S)-7-[4,6,7,8-tetra-(4-isopropylthiophenyl)quinoline-3-yl]-3,5-dihydroxy-6(E)-heptenoic acid,
(3R,5S)-7-[6-fluoro-7-chloro-4-(3-methoxythiophenyl)quinoline-3-yl]-3,5-dihydroxy-6(E)-heptenoic acid,
(3R,5S)-7-[6-fluoro-4,7-di-(3-methoxythiophenyl)quinoline-3-yl]-3,5-dihydroxy-6(E)-heptenoic acid,
(3R,5S)-7-[6-fluoro-7-chloro-4-(4-fluorophenoxy)quinoline-3-yl]-3,5-dihydroxy-6(E)-heptenoic acid hemi calcium salt,
(3R,5S)-7-[6-fluoro-7-chloro-4-(3-methoxythiophenyl)quinoline-3-yl]-3,5-dihydroxy-6(E)-heptenoic acid hemi calcium salt,
(3R,5S)-7-[6-fluoro-4,7-di-thiophenyl-quinoline-3-yl]-3,5-dihydroxy-6(E)-heptenoic acid hemi calcium salt,
(3R,5S)-7-[6-fluoro-4,7-di-(3-methoxythiophenyl)quinoline-3-yl]-3,5-dihydroxy-6(E)-heptenoic acid hemi calcium salt,
(3R,5S)-7-[6-fluoro-4,7-di-(4-isopropylthiophenyl)quinoline-3-yl]-3,5-dihydroxy-6(E)-heptenoic acid hemi calcium salt,
(3R,5S)-7-[6,7,8-trifluoro-4-(4-fluorothiophenyl)quinoline-3-yl]-3,5-dihydroxy-6(E)-heptenoic acid hemi calcium salt, (3R,5S)-7-[6,7,8-trifluoro-4-(4-isopropylthiophenyl)quinoline-3-yl]-3,5-dihydroxy-6(E)-heptenoic acid hemi calcium salt,
(3R,5S)-7-[6,8-di-fluoro-4,7-di-phenoxyquinoline-3-yl]-3,5-dihydroxy-6(E)-heptenoic acid hemi calcium salt, or
(3R,5S)-7-[4,6,7,8-tetra-phenoxyquinoline-3-yl]-3,5-dihydroxy-6(E)-heptenoic acid hemi calcium salt.

According to the present invention, the pharmaceutically acceptable solvate is a hydrate, and solvate with C1~4 alcohol or other organic solvents.

Wherein
M is Na$^+$, NH$_4^+$ or Ca$^{2+}$;

Method 2 comprising steps of preparing a compound represented by Formula A by hydrolysis of a compound represented by Formula B under the action of an alkaline in an organic solvent, adjusting pH value to 7~7.5 by addition of an acid and then adding a calcium salt, wherein said alkaline is sodium hydroxide, potassium hydroxide, or ammonia-alcoholic solution,

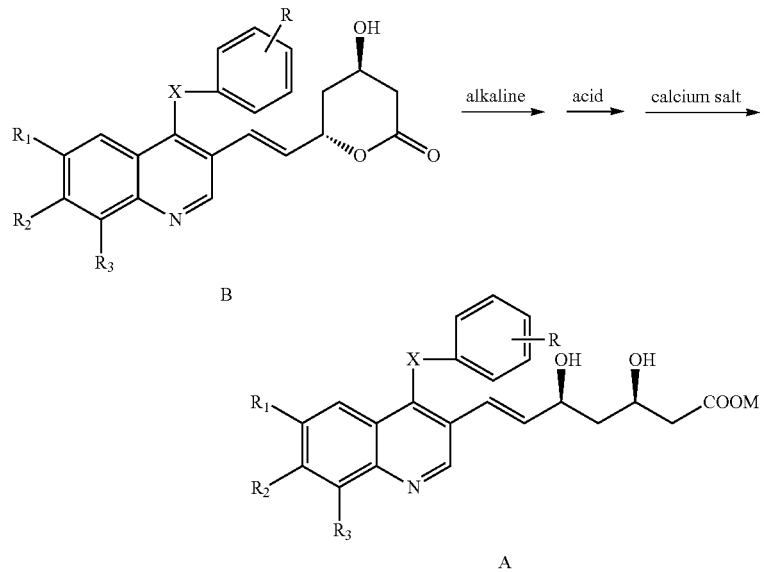

The second object of present invention is to provide a preparation method of the quinoline compound or pharmaceutically acceptable solvate, optical isomer or polymorph thereof. The preparation method may be selected from any one of the following five methods:

Method 1 comprising steps of preparing a compound represented by Formula A by hydrolysis of a compound represented by Formula B under the action of an alkaline in an organic solvent, wherein said alkaline is sodium hydroxide, ammonia-alcohol solution, or calcium hydroxide, Wherein
M is Ca$^{2+}$;

Method 3 comprising steps of preparing a compound represented by Formula A by hydrolysis of a compound represented by Formula B under the action of an alkaline in an organic solvent and then adjusting pH value to 2~3 by addition of an acid, wherein said alkaline is sodium hydroxide, ammonia-alcoholic solution, or calcium hydroxide,

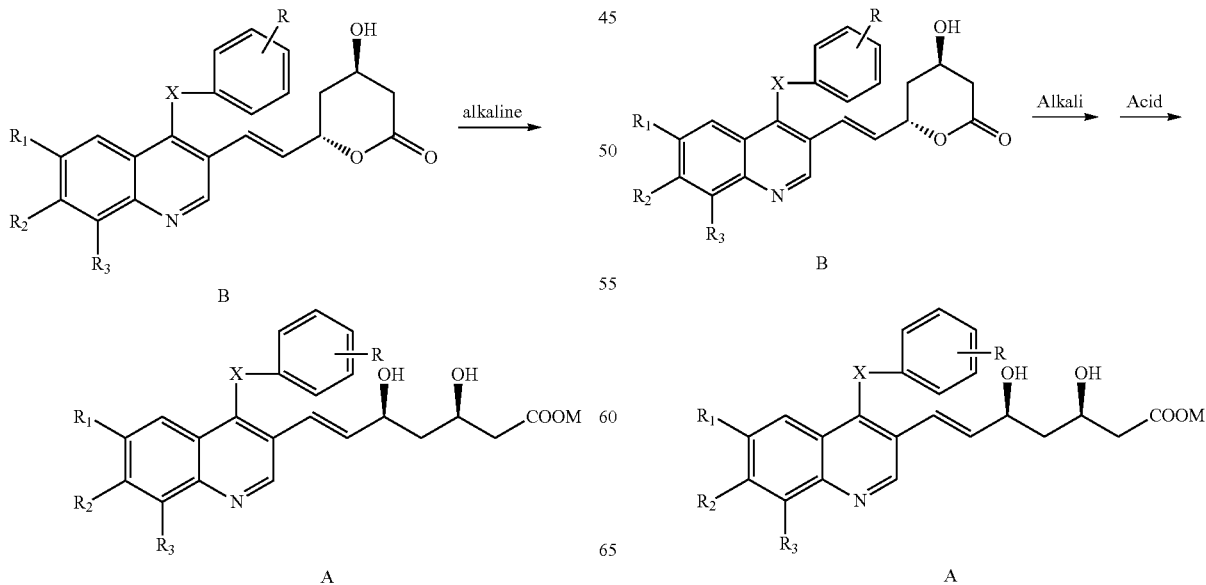

Wherein
M is H;

Method 4 comprising step of preparing a compound represented by Formula A by reaction of an alkaline and a compound represented by Formula C in an organic solvent, wherein said alkaline is sodium hydroxide, ammonia-alcoholic solution, or calcium hydroxide,

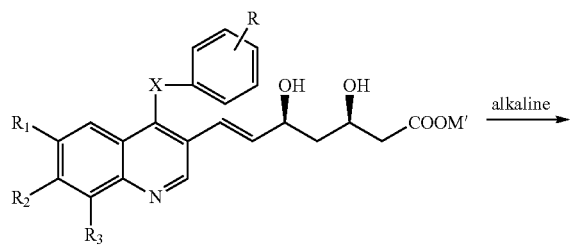

C

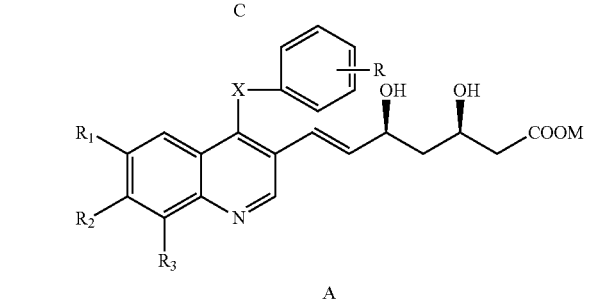

A

Wherein
M' is H, and M is Na$^+$, NH$_4^+$, or Ca$^{2+}$; and

Method 5 comprising step of preparing a compound represented by Formula A by reaction of a calcium salt and a compound represented by Formula C in an organic solvent or water,

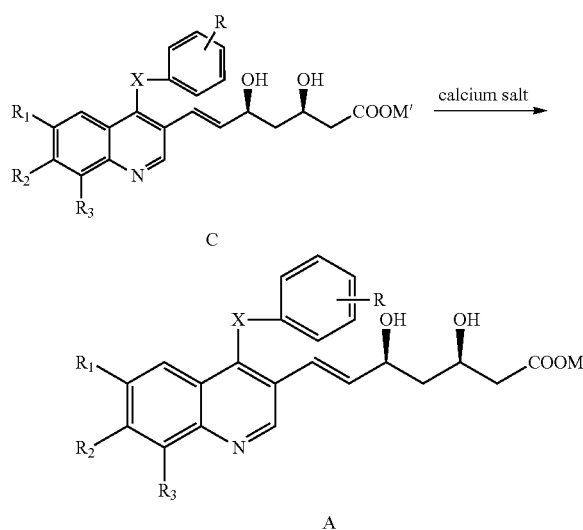

Wherein
M' is Na$^+$ or NH$_4^+$, and M is Ca$^{2+}$;
Wherein
in the formula representing each of the compounds in above five methods,
X is S or O;
each of R$_1$, R$_2$ and R$_3$ is independently H, halogen, a substituent represented by the group shown in Formula D or Formula E;

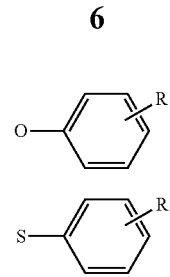

Wherein
R is H hydrogen, halogen, C$_1$-C$_4$ alkyl, or C$_1$-C$_4$ alkoxy.

Method 1 according to the present invention comprises steps of preparing a compound represented by Formula A by hydrolysis of a compound represented by Formula B under the action of an alkaline in an organic solvent, wherein said alkaline is sodium hydroxide, ammonia-alcohol solution, or calcium hydroxide, and M in the formula is Na$^+$, NH$_4^+$ or Ca$^{2+}$. In this method, said organic solvent is one or more selected from the group consisting of tetrahydrofuran (THF), methyltertbutyl ether, dichloromethane, trichloromethane, toluene, methanol, ethanol, t-butanol, isopropanol, acetone and acetonitrile, and the most preferable is methanol. The reaction temperature ranges from 0° C. to 80° C., preferably from 0° C. to 25° C., and the reaction time ranges from 10 min to 8 h.

Method 2 according to the present invention comprises steps of preparing a compound represented by Formula A by hydrolyzing a compound represented by Formula B under the action of an alkaline in an organic solvent, adjusting pH value to 7 to 7.5 by addition of an acid and then adding a calcium salt, wherein said alkaline is sodium hydroxide, potassium hydroxide, or ammonia-alcoholic solution, and M is Ca$^{2+}$. According to the present invention, said compound represented by Formula B can be prepared by one of the methods disclosed in Chinese patent application No. 200610148118.4 and No. 200710036427.7. Said acid is HCl, H$_2$SO$_4$, CH$_3$COOH or CF$_3$COOH. Said calcium salt is preferably CaCl$_2$ or Ca(CH$_3$COO)$_2$; said organic solvent is one or more selected from the group consisting of tetrahydrofuran (THF), methyltertbutyl ether, dichloromethane, trichloromethane, toluene, methanol, ethanol, t-butanol, isopropanol, acetone and acetonitrile, and the most preferably is methanol. The reaction temperature ranges from 0° C. to 80° C., preferably from 0° C. to 25° C., and the reaction time ranges from 10 min to 8 h.

Method 3 according to the present invention comprises steps of preparing a compound represented by Formula A by hydrolyzing a compound represented by Formula B under the action of an alkaline in an organic solvent and then adjusting pH value to 2~3 by addition of an acid, wherein said alkaline is sodium hydroxide, ammonia-alcohol solution, or calcium hydroxide, and M is H. According to the present invention, said compound represented by Formula B can be prepared using one of the methods disclosed in Chinese patent application No. 200610148118.4 and No. 200710036427.7. Said acid preferably is HCl, H$_2$SO$_4$, CH$_3$COOH or CF$_3$COOH, and the most preferably is HCl. Said organic solvent is one or more selected from the group consisting of tetrahydrofuran (THF), methyltertiarybutyl ether, dichloromethane, trichloromethane, toluene, methanol, ethanol, t-butanol, isopropanol, acetone and acetonitrile, and the most preferably is methanol. The reaction temperature ranges from 0° C. to 80° C., preferably from 0° C. to 25° C., and the reaction time ranges from 10 min to 8 h.

Method 4 according to the present invention comprises steps of preparing a compound represented by Formula A by reaction of an alkaline and a compound represented by Formula C in an organic solvent, wherein said alkaline is sodium hydroxide, ammonia-alcohol solution, or calcium hydroxide. M' is H. M is Na, $NH_4^+$ or $Ca^{2+}$. According to the present invention, said compound represented by Formula C can be prepared by using the above mentioned method 3, said organic solvent is preferably one or more selected from the group consisting of tetrahydrofuran (THF), methyltertbutyl ether, dichloromethane, trichloromethane, and toluene, and the most preferably is tetrahydrofuran (THF). The reaction temperature ranges from 0° C. to 80° C., preferably 25° C., and the reaction time ranges from 10 min to 8 h.

Method 5 according to the present invention comprises steps of preparing a compound represented by Formula A by reaction of a calcium salt and a compound represented by Formula C in an organic solvent or water, wherein M' is $Na^+$ or $NH_4^+$, and M is $Ca^{2+}$. According to the present invention, said compound represented by Formula C can be prepared by using the above-mentioned method 1; said calcium salt is $CaCl_2$ or $Ca(CH_3COO)_2$, and the most preferably is $CaCl_2$; said organic solvent is preferably one or more selected from the group consisting of tetrahydrofuran (THF), methyltertbutyl ether, dichloromethane, trichloromethane, and toluene, and the most preferably is tetrahydrofuran (THF). The reaction temperature ranges from 0° C. to 80° C., preferably 25° C., and the reaction time ranges from 10 min to 8 h.

The third object of the present invention is to provide a pharmaceutical composition comprising any one of the treatment effective amount of the quinoline compound represented by Formula A, or pharmaceutically acceptable solvate, optical isomer or polymorph thereof and a pharmaceutically acceptable carrier.

The quinoline compound or pharmaceutically acceptable solvate, optical isomer or polymorph thereof according to the present invention as well as a pharmaceutically acceptable carrier can be applied in a form of composition to a patient who needs to be treated. Said pharmaceutically acceptable carrier refers to a medicine carrier commonly used in the pharmaceutical field including diluents, excipients such as water etc., adhesives such as a cellulose derivative, gelatin, polyvinylpyrrolidone etc., fillers such as a starch etc., disintegrating agent such as calcium carbonate, sodium hydrogen carbonate. Besides, other auxiliary agents such as aroma agents and/or sweetening agents can be added in the composition.

The pharmaceutical composition according to the present invention can be prepared by using ordinary methods in the art. The quinoline compound or pharmaceutically acceptable solvate, optical isomer or polymorph thereof of the present invention as an active ingredient, as well as a pharmaceutically acceptable carrier can be manufactured in various kinds of dosage forms. In an oral formulation, it can be manufactured as a regular solid preparation such as tablet, powder or capsule etc. In an injection formulation, it can be manufacture as an injection solution. In all kinds of dosage forms, the content of the active ingredient is 0.1% to 99.9% by weight, preferably 0.5% to 90% by weight.

The pharmaceutical composition according to the present invention can be administered to a patient who needs to be treated by intravenous injection, subcutaneous injection or oral administration. The dosage administered to a patient is 1-1000 mg/kg body weight/day and can vary according to the patient's age and patient's condition.

The fourth object of the present invention is to provide an application of the quinloline compound or pharmaceutically acceptable solvate, optical isomer or polymorphs thereof, or the pharmaceutical composition comprising the same in manufacturing a medicament for inhibiting 3-hydroxy-3-methylglutaryl-coenzyme (HMG-CoA) reductase or for the treatment and prophylaxis of a disease which can be treated effectively by inhibiting 3-hydroxy-3-methylglutaryl-coenzyme A (HMG-CoA) reductase, wherein said disease is hypercholesterolemia, hyperlipidemia, atherosclerosis or cardiovascular disease.

All agents used in the present invention are available in the market.

Compared to the prior art, the advantageous effects of present invention is that the quinoline compound according to the present invention has an excellent lipid reduction effect in vivo and can be applied for the treatment of a hyperlipidemia related disease.

EMBODIMENTS OF THE INVENTION

The present invention will be further demonstrated in the following description of exemplary embodiments which are given for illustration of said invention and are not intended to be limited thereof.

Experimental conditions not described in the following examples shall refer to the regular experimental conditions, or the conditions suggested by the manufacturer.

The present invention will be further illustrated in combination of the following examples but the present invention is not limited to the examples.

EXAMPLE 1

(3R,5S)-7-[4,6,7,8-tetra-(4-isopropylthiophenyl) quinoline-3-yl]-3,5-dihydroxy-6(E)-heptenoic acid
(A1)

0.5 g of (4R,6S)-6-[(E)-2-(4,6,7,8-tetra-4-isopropylthiophenyl quinoline-3-)ethenyl]-3,4,5,6-tetrahydro-4-hydroxy-2H-pyran-2-one (0.58 mmol) and 5 ml of THF (tetrahydrofuran) are mixed and cooled to 0° C., and then 0.8 ml of 1N NaOH (0.8 mmol) is added, and then stirring for 1 hour. The pH value of the resulting solution is adjusted to be 2 by adding 1N HCl at 0° C. Then the resulting solution is concentrated under reduced pressure, water and ethyl acetate are added into the residue, and then the organic layer is separated. The aqueous layer is extracted three times with ethyl acetate and then is merged into the organic layer. The resulting organic layer is washed with water till neutral. Then it is dried by anhydrous $Na_2SO_4$, and concentrated to obtain 0.4 g of solid product. The yield is 78%, Mp (Melting Point): 118° C.-120° C., $[\alpha]_D^{26}$=18.2 (c 1, THF). $^1$H NMR (400 MHz, DMSO-$d_6$) δ 1.17-1.11 (m, 18H), 1.25 (d, 6H, J=6.8 Hz), 1.62-1.53 (m, 2H), 2.29-2.12 (m, 2H), 2.86-2.74 (m, 3H), 3.03-2.94 (m, 1H), 3.93-3.92 (m, 1H), 4.37-4.34 (m, 1H), 6.72-6.64 (m, 3H), 6.88 (d, 2H, J=8.4 Hz), 7.14-7.00 (m, 8H), 7.34-7.14 (m, 5H), 7.83 (s, 1H), 9.13 (s, 1H); TOF MS (ES+): 1775 (2M+H), 888 (M+H); TOF MS (ES−): 1773 (2M−H), 886 (M−H).

EXAMPLE 2

(3R,5S)-7-[6-fluoro-7-chloro-4-(3-methoxylthiophenyl)quinoline-3-yl]-3,5-dihydroxy-6(E)-heptenoic acid (A2)

0.27 g of (4R,6S)-6-[(E)-2-(6-fluoro-7-chloro-4-(3-methoxythiophenyl) quinoline-3-yl)ethenyl]-3,4,5,6-tetrahydro- 4-hydroxy-2H-pyran-2-one (0.58 mmol) and 5 ml of methanol are mixed and cooled to 10° C., and then 0.8 ml of 1N KOH (0.8 mmol) is added, and then stirring for 5 hours. The pH value of the resulting solution is adjusted to be 2 by adding 1N HCl at 25° C. Then the resulting solution is concentrated under reduced pressure, water and ethyl acetate are added into the residue, then the organic layer is separated. The aqueous layer is extracted three times by ethyl acetate and then is merged into the organic layer. The resulting organic layer is washed with water till neutral. Then it is dried by anhydrous $Na_2SO_4$, and concentrated to obtain 0.26 g of solid product. The yield is 94.7%, and Mp: 178° C.-180° C., $[\alpha]_D^{26}$=31.8 (c 1, methanol). $^1$H NMR (400 MHz, DMSO-$d_6$) δ 1.69-1.59 (m, 2H), 2.42-2.25 (m, 2H), 3.67 (s, 3H), 4.04-4.01 (m, 1H), 4.39-4.37 (m, 1H), 6.57 (d, 1H, J=8.0 Hz), 6.81-6.69 (m, 3H), 7.16 (t, 1H, J=8.0 Hz), 7.28 (d, 1H, J=16.0 Hz), 8.13 (d, 1H, J=10.8 Hz), 8.33 (d, 1H, J=7.2 Hz), 9.3 (s, 1H) 12.1-11.9 (brs, 1H); TOF MS (ES+): 478 (M+H); TOF MS (ES−): 476 (M−H).

EXAMPLE 3

(3R,5S)-7-[6-fluoro-4,7-di-(3-methoxylthiophenyl) quinoline-3-yl]-3,5-dihydroxy-6(E)-heptenoic acid (A3)

At 25° C., 0.8 ml of 1N NaOH (0.8 mmol) is added into the solution of 0.33 g of (4R,6S)-6-[(E)-2-(6-fluoro-4,7-di-(3-methoxythiophenyl)quinoline-3-yl)ethenyl]-3,4,5,6-tetrahydro-4-hydroxy-2H-pyran-2-one (0.58 mmol) dissolved in 5 ml of acetone, and then stirring for 8 hours. The pH value of the resulting solution is adjusted to 2 by adding with 1N HCl at 0° C. Then the resulting solution is concentrated under reduced pressure. Water and ethyl acetate are added into the residue and the organic layer is separated. The aqueous layer is extracted three times by ethyl acetate and then is merged into the organic layer. The resulting organic layer is washed with water till neutral. Then it is dried by anhydrous $Na_2SO_4$, and concentrated to obtain 0.29 g of solid product. The yield is 85.3%, and Mp: 154° C.-156° C., $[\alpha]_D^{26}$=21.6 (c 1, methanol). $^1$H NMR (400 MHz, DMSO-$d_6$) δ 1.68-1.58 (m, 2H), 2.5-2.24 (m, 2H), 3.67 (s, 3H), 3.78 (s, 3H), 4.01 (brs, 1H), 4.36 (brs, 1H), 4.69 (brs, 1H, disappears on $D_2O$ exchange), 5.05 (d, 1H, J=4.0 Hz, disappears on $D_2O$ exchange), 6.56 (d, 1H, J=7.6 Hz), 6.78-6.67 (m, 3H), 7.18-7.07 (m, 4H), 7.26 (d, 1H, J=15.6 Hz), 7.44 (t, 1H, J=7.6 Hz), 7.60 (d, 1H, J=7.6 Hz), 8.00 (d, 1H, J=11.2 Hz), 9.13 (s, 1H), 11.9 (brs, 1H, disappears on $D_2O$ exchange); TOF MS (ES+): 582 (M+H); TOF MS (ES−): 580 (M−H).

EXAMPLE 4

(3R,5S)-7-[6-fluoro-4,7-di-(thiophenyl)quinoline-3-yl]-3,5-dihydroxy-6(E)-heptenoic acid ammonium salt (A4)

According to the method of Example 1, the solid of (3R,5S)-7-[6-fluoro-4,7-di-(thiophenyl)quinoline-3-yl]-3,5-dihydroxy-6(E)-heptenoic acid is prepared from (4R,6S)-6-[(E)-2-(6-fluoro-4,7-di-(thiophenyl)quinoline-3-yl)ethenyl]-3,4,5,6-tetrahydro-4-hydroxy-2H-pyran-2-one.

A turbid solution is prepared by adding 0.5 g of the above-prepared solid into 10 ml of methanol. The solution is gradually dissolved by adding 10 ml of ammonia-methanol (18.5 wt % of ammonia), and then stirred for 30 min at room temperature. The resulting solution is concentrated under reduced pressure to obtain 0.48 g of oil. Recrystallize the oil with ethyl acetate and ethanol to obtain 0.39 g of a white solid. The yield is 74%, and Mp: 142° C.-144° C., $[\alpha]_D^{26}$=13.4 (c 1, methanol). $^1$H NMR (400 MHz, DMSO-$d_6$) δ 1.18 (s, 4H), 1.61-1.48 (m, 2H), 2.29-2.10 (m, 2H), 3.96-3.89 (m, 1H), 4.37-4.33 (m, 1H), 6.70 (dd, 1H, J=16.4, 5.6 Hz), 7.09-7.07 (m, 2H), 7.18 (t, 1H, J=8.4 Hz), 7.28-7.23 (m, 3H), 7.59-7.51 (m, 5H), 8.00 (d, 1H, J=11.2 Hz), 9.17 (s, 1H); TOF MS (ES+): 522 (M+H), 544 (M+Na), 1043 (2M+H); TOF MS (ES−): 520 (M−H), 1041 (2M−H).

EXAMPLE 5

(3R,5S)-7-[6-fluoro-4,7-di-(3-methoxythiophenyl) quinoline-3-yl]-3,5-dihydroxy-6(E)-heptenoic acid hemi calcium salt (A5)

0.7 g of (4R,6S)-6-[(E)-2-(6-fluoro-4,7-di-(3-methoxythiophenyl)quinoline-3-)ethenyl]-3,4,5,6-tetrahydro-4-hydroxy-2H-pyran-2-one (1.2 mmol) and 7 ml of ethanol are mixed and cooled to 0° C., and then 1.5 ml of 1N KOH (1.5 mmol) is added, and stirring for 2 hours. The pH value of the resulting solution is adjusted to be 7-8 by adding 1N HCl at 0° C. Then it is concentrated under reduced pressure to remove the solvent, followed by adding of 10 ml of water, and then stirring till it is dissolved. 0.14 g of $CaCl_2$ is added into the resulting solution and then stirring overnight. The precipitate is collected by filtration and washed with water to obtain a solid. The resulting solid is dried in vacuum for 24 hours to obtain 0.6 g of light yellow solid. The yield is 80%. Mp: 156° C. (dec). $[\alpha]_D^{26}$=3 (c 1, THF). $^1$H NMR (400 MHz, DMSO-$d_6$) δ 1.63-1.51 (m, 2H), 2.18-1.97 (m, 2H), 3.67 (s, 3H), 3.78 (s, 3H), 3.89-3.86 (m, 1H), 4.39-4.36 (m, 1H), 6.55 (d, 1H, J=8.0 Hz), 6.77-6.65 (m, 3H), 7.18-7.06 (m, 4H), 7.24 (d, 1H, J=16.0 Hz), 7.43 (t, 1H, J=8.4 Hz), 7.61 (d, 1H, J=7.2 Hz), 7.99 (d, 1H, J=6.0 Hz), 9.17 (s, 1H); TOF MS (ES+): 1201 (M+H), 1163 [(M−Ca)+3H], 582 [(M−Ca)/2+2H]; TOF MS (ES−): 1161 [(M−Ca)+H], 580 (M−Ca)/2.

EXAMPLE 6

(3R,5S)-7-[6,7,8-trifluoro-4-(4-isopropylthiophenyl) quinoline-3-yl]-3,5-dihydroxy-6(E)-heptenoic acid hemi calcium salt (A6)

At 25° C., 1.5 ml of 1N KOH (1.5 mmol) is dropped into a solution of 0.57 g of (4R,6S)-6-[(E)-2-(6,7,8-trifluoro-4-(4-isopropylthiophenyl)quinoline-3-yl)ethenyl]-3,4,5,6-tetrahydro-4-hydroxy-2H-pyran-2-one (1.2 mmol) dissolved in 7 ml of acetonitrile, and stirring for 1 hour. The pH value of the resulting mixture is adjusted to 7-8 by adding 1N HCl at 0° C. Then it is concentrated under reduced pressure to remove the solvent, followed by adding 10 ml of water. The resulting solution is added with 0.26 g of $Ca(CH_3COO)_2 \cdot H_2O$ aqueous solution and stirred overnight. The precipitate is collected by filtration and washed with water. The resulting solids is dried in vacuum for 24 hours to obtain 0.49 g of solid. The yield is 80%. Mp: 118° C. to 119° C., $[\alpha]_D^{26}$=15.3 (c 1, THF). $^1$H NMR (400 MHz, DMSO-$d_6$) δ 1.64-1.10 (m, 6H), 1.68-1.61 (m, 2H), 2.43-2.26 (m, 2H), 2.84-2.71 (m, 1H), 4.06-4.02 (m, 1H), 4.41-4.37 (m, 1H), 6.77 (dd, 1H, J=16.4, 5.2 Hz), 7.16-7.05 (m, 4H), 7.31 (dd, 1H, J=16.4, 4.0 Hz), 8.12-8.07 (m, 1H), 9.32 (s, 1H); TOF MS (ES+): 2042 (2M+2H), 1021 (M+1), 492 [(M−Ca)/2+2H].

EXAMPLE 7

(3R,5S)-7-[6,7,8-trifluoro-4-(4-fluorothiophenyl) quinoline-3-yl]-3,5-dihydroxy-6(E)-heptenoic acid sodium salt (A7)

0.43 g of (4R,6S)-6-[(E)-2-(6,7,8-trifluoro-4-(4-fluorothiophenyl)quinoline-3-yl)ethenyl]-3,4,5,6-tetrahydro-4- hydroxy-2H-pyran-2-one (0.96 mmol) and 10 ml of methanol are mixed and cooled to 0° C., and then 1.4 ml of 1N NaOH (1.4 mmol) is added, and reacting for 1 hour. The resulting solution is concentrated under reduced pressure. The resulting crude product is recrystallized with ethanol and water to obtain 0.3 g of solid. The yield is 64.2%. Mp: 102° C.-104° C., $[\alpha]_D^{26}$=10.8 (c 1, methanol). $^1$H NMR (400 MHz, DMSO-$d_6$) δ 1.62~1.45 (m, 2H), 2.12-1.87 (m, 2H), 3.81 (t, 1H, J=4.0 Hz), 4.39 (d, 1H, J=2.8 Hz), 6.75 (dd, 1H, J=16.0, 4.8 Hz), 7.28-7.09 (m, 5H), 8.13-8.08 (m, 1H), 9.30 (s, 1H); TOF MS (ES+): 490 (M+H), 512 (M+Na), 1001 (2M+Na).

EXAMPLE 8

(3R,5S)-7-[6,7,8-trifluoro-4-(4-fluorothiophenyl) quinoline-3-yl]-3,5-dihydroxy-6(E)-heptenoic acid hemi calcium salt (A8)

(3R,5S)-7-[6,7,8-trifluoro-4-(4-fluorothiophenyl)quinoline-3-yl]-3,5-dihydroxy-6(E)-heptenoic acid sodium salt (3 g, 6 mmol) is dissolved in water 30 ml. Into the resulting solution, CaCl$_2$ aqueous solution (1 g, 9 mmol) is added, and stirring at room temperature for 2 hours, followed by filtration and washing with water to obtain 2.6 g of (3R,5S)-7-[6,7,8-trifluoro-4-(4-fluorothiophenyl)quinoline-3-yl]-3,5-dihydroxy-6(E)-heptenoic acid hemi calcium salt. The yield is 90%. Mp: 172° C. (dec), $[z]_D^{26}$=10.8 (c 1, THF). $^1$H NMR (400 MHz, DMSO-$d_6$) δ 1.66-1.52 (m, 2H), 2.24-2.06 (m, 2H), 3.96-3.94 (m, 1H), 4.42-4.37 (m, 1H), 6.76-6.71 (dd, 1H, J=16.4, 5.2 Hz), 7.27-7.07 (m, 5H), 8.06-8.02 (m, 1H), 9.24 (s, 1H); TOF MS (ES+): 1946 (2M+2H), 973 (M+1), 582 [(M−Ca)/2+2H]; TOF MS (ES−): 933 [(M−Ca)+H], 466 (M−Ca)/2.

EXAMPLE 9

(3R,5S)-7-[4,6,7,8-tetra-phenoxyquinoline-3-yl]-3,5-dihydroxy-6(E)-heptenoic acid hemi calcium salt (A9)

At 10° C., 1.5 ml of 1N KOH (1.5 mmol) is dropped into a solution of 0.76 g of (4R,6S)-6-[(E)-2-(4,6,7,8-tetra-phenoxyquinoline-3-)ethenyl]-3,4,5,6-tetrahydro-4-hydroxy-2H-pyran-2-one (1.2 mmol) dissolved in 15 ml of methyltertbutyl ether, and stirring for 8 hours. Into the resulting mixture, 1N HCl is added at 0° C. to adjust the pH value to 7-8. Then the resulting solution is concentrated under reduced pressure to remove the organic solvent, followed by adding 10 ml of water. Into the resulting solution, 0.26 g of Ca(CH$_3$COO)$_2$.H$_2$O aqueous solution is added, and stirring overnight. The precipitate is collected by filtration and washed with water. The resulting solids are dried in vacuum for 24 hours to obtain 0.66 g of solids. The yield is 81%. Mp: 140° C. (dec), $[\alpha]_D^{26}$=13.9 (c 1, THF). $^1$H NMR (400 MHz, DMSO-$d_6$) δ 1.64-1.49 (m, 2H), 2.37-2.20 (m, 2H), 3.97-3.91 (m, 1H), 4.28-4.24 (m, 1H), 4.95 (br, 1H), 6.85-6.79 (m, 8H), 6.68-6.66 (m, 3H), 7.00-6.96 (m, 2H), 7.13-7.05 (m, 3H), 7.31-7.21 (m, 7H), 9.09 (s, 1H); TOF MS (ES+): 1349 (M+H), 1311 [(M−Ca)+3H], 656 [(M−Ca)/2+2H].

EXAMPLE 10

(3R,5S)-7-[6-fluoro-4,7-di-(thiophenyl)quinoline-3-yl]-3,5-dihydroxy-6(E)-heptenoic acid hemi calcium salt (A10)

At 0° C., 1.5 ml of 1N NaOH (1.5 mmol) is dropped into a solution of 0.6 g of (4R,6S)-6-[(E)-2-(6-fluoro-4,7-di-(thiophenyl)quinoline-3-)ethenyl]-3,4,5,6-tetrahydro-4-hydroxy-2H-pyran-2-one (1.2 mmol) and 15 ml of methanol and stirred for 1 hour. The resulting solution is added with 1N HCl at 0° C. and the pH value is adjusted to 7-8. Then it is concentrated under reduced pressure to remove the organic solvent, followed by addition of 10 ml of water. Into the resulting solution, 0.14 g of CaCl$_2$ aqueous solution is added and stirred overnight. The precipitate is collected by filtration and washed with water. The resulting solids is dried in vacuum for 24 hours to obtain 0.49 g of solids. The yield is 75%. Mp: 136-138° C., $[\alpha]_D^{26}$=−13.3 (c 1, methanol). $^1$H NMR (400 MHz, DMSO-$d_6$) δ 1.66-1.56 (m, 2H), 2.37-2.20 (m, 2H), 4.02-3.95 (m, 1H), 4.38-4.34 (m, 1H), 6.70 (dd, 1H, J=16.4, 4.8 Hz), 7.08 (d, 2H, J=7.2 Hz), 7.18 (t, 1H, J=6.8 Hz), 7.26 (t, 3H, J=7.2 Hz), 7.59-7.51 (m, 5H), 7.99 (d, 1H, J=11.6 Hz), 9.17 (s, 1H); TOF MS (ES+): 1081 (M+H), 1043 [(M−Ca)+3H], 522 [(M−Ca)/2+H]; TOF MS (ES−): 1041 [(M−Ca)+H], 520 (M−Ca)/2.

EXAMPLE 11

(3R,5S)-7-[6-fluoro-7-chloro-4-(3-methoxythiophenyl)quinoline-3-yl]-3,5-dihydroxy-6(E)-heptenoic acid hemi calcium salt (A11)

According to the method of Example 5, (3R,5S)-7-[6-fluoro-7-chloro-4-(3-methoxythiophenyl)quinoline-3-yl]-3,5-dihydroxy-6(E)-heptenoic acid hemi calcium salt is prepared from (4R,6S)-6-[(E)-2-(6-fluoro-7-chloro-4-(3-methoxythiophenyl)quinoline-3-)ethenyl]-3,4,5,6-tetrahydro-4-hydroxy-2H-pyran-2-one. The yield is 82%. Mp: 176° C. (dec), $[\alpha]_D^{26}$=16.8 (c 1, THF:H$_2$O=2:1). $^1$H NMR (400 MHz, DMSO-$d_6$) δ 1.65-1.54 (m, 2H), 2.24-2.05 (m, 2H), 3.65 (s, 3H), 3.97-3.93 (m, 1H), 4.40-4.37 (m, 1H), 6.54-6.52 (m, 1H), 6.65 (t, 1H, J=2.0 Hz), 6.78-6.72 (m, 2H), 7.13 (t, 1H, J=8.0 Hz), 7.30 (dd, 1H, J=16.0, 1.2 Hz), 8.06 (d, 1H, J=10.8 Hz), 8.23 (d, 1H, J=3.8 Hz), 9.24 (s, 1H); TOF MS (ES+): 993 (M+H), 478 [(M−Ca)/2+2H].

EXAMPLE 12

(3R,5S)-7-[6,8-difluoro-4,7-di-(phenoxy)quinoline-3-yl]-3,5-dihydroxy-6(E)-heptenoic acid hemi calcium salt (A12)

According to the method of Example 5, (3R,5S)-7-[6,8-difluoro-4,7-di-(phenoxy)quinoline-3-yl]-3,5-dihydroxy-6(E)-heptenoic acid hemi calcium salt is prepared from (4R,6S)-6-[(E)-2-(6,8-difluoro-4,7-di-(phenoxy)quinoline-3-)ethenyl]-3,4,5,6-tetrahydro-4-hydroxy-2H-pyran-2-one. The yield is 82%. Mp: 146-148° C., $[\alpha]_D^{26}$=17.7 (c 1, THF:H$_2$O=2:1). $^1$H NMR (400 MHz, DMSO-$d_6$) δ 1.66-1.56 (m, 2H), 2.37-2.20 (m, 2H), 4.01-3.95 (m, 1H), 4.38-4.34 (m, 1H), 6.70 (dd, 1H, J=16.0, 5.2 Hz), 7.28-7.07 (m, 6H), 7.59-7.51 (m, 5H), 7.99 (d, 1H, J=11.2 Hz), 9.16 (s, 1H); TOF MS (ES+): 2105 (2M+H), 1053 (M+1), 508 [(M−Ca)/2+2H].

EXAMPLE 13

(3R,5S)-7-[6-fluoro-4,7-di-(4-isopropylthiophenyl) quinoline-3-yl]-3,5-dihydroxy-6(E)-heptenoic acid hemi calcium salt (A13)

According to the method of Example 5, (3R,5S)-7-[6-fluoro-4,7-di-(4-isopropylthiophenyl)quinoline-3-yl]-3,5-dihydroxy-6(E)-heptenoic acid hemi calcium salt is prepared from (4R,6S)-6-[(E)-2-(6-fluoro-4,7-di-(4-isopropylthiophenyl)quinoline-3-)ethenyl]-3,4,5,6-tetrahydro-4-hydroxy-2H-pyran-2-one. The yield is 78%. Mp: 206-209° C., $[\alpha]_D^{26}$=7.0 (c 1, THF). $^1$H NMR (400 MHz, DMSO-d$_6$) δ 1.09 (d, 6H, J=6.8 Hz), 1.22 (d, 6H, J=6.8 Hz), 1.61-1.55 (m, 2H), 2.24-2.06 (m, 2H), 2.77-2.74 (m, 1H), 2.96-2.92 (m, 1H), 3.97-3.95 (m, 1H), 4.37-4.36 (m, 1H), 6.65 (dd, 1H, J=16.0, 5.2 Hz), 6.97 (d, 2H, J=8.0 Hz), 7.08 (d, 2H, J=8.0 Hz), 7.24 (d, 1H, J=16.0 Hz), 7.37 (d, 2H, J=8.0 Hz), 7.41 (d, 1H, J=7.2 Hz), 7.48 (d, 2H, J=8.0 Hz), 7.94 (d, 2H, J=11.2 Hz), 9.07 (s, 1H); TOF MS (ES+): 1249 (M+1), 606 [(M−Ca)/2+2H].

EXAMPLE 14

(3R,5S)-7-[6-fluoro-7-chloro-4-(4-fluorophenoxy) quinoline-3-yl]-3,5-dihydroxy-6(E)-heptenoic acid hemi calcium salt (A14)

According to the method of Example 5, (3R,5S)-7-[6-fluoro-7-chloro-4-(4-fluorophenoxy)quinoline-3-yl]-3,5-dihydroxy-6(E)-heptenoic acid hemi calcium salt is prepared from (4R,6S)-6-[(E)-2-(6-fluoro-7-chloro-4-(4-fluorophenoxy)quinoline-3-)ethenyl]-3,4,5,6-tetrahydro-4-hydroxy-2H-pyran-2-one. The yield is 87%. Mp: 158-160° C., $[\alpha]_D^{26}$=20.0 (c 1, THF:H$_2$O=2:1). $^1$H NMR (400 MHz, DMSO-d$_6$) δ 1.62-1.54 (m, 2H), 2.37-2.20 (m, 2H), 3.96-3.92 (m, 1H), 4.30-4.28 (m, 1H), 6.76-6.65 (m, 2H), 6.92-6.90 (m, 2H), 7.17-7.13 (m, 2H), 7.65 (d, 1H, J=10.0 Hz), 8.33 (d, 1H, J=7.2 Hz), 9.26 (s, 1H); TOF MS (ES+): 937 (M+H), 450 [(M−Ca)+2H].

Below is a further illustration of the advantages of the present invention by the experiments.

Effect Example 1

Lipid-lowering in vivo experiments are made in hyperlipidemia quail with the compounds A14, A6, A5, A1, A10, A8, A9, A11, A12, A13 according to the present invention. Atorvastatin (20 mg/kg) were used as the positive control. Two groups of dosage (Low: 5 mg/kg, High: 20 mg/kg) of the ten compounds of A14, A6, A5, A1, A10, A8, A9, A11, A12, A13 were tested. After one week feeding with normal diet, except for the normal control group, the model control group and the tested groups of quails were fed with hypercholesterol diet for four weeks, and then the blood was collected respectively for testing the content of lipidemia including triglyceride, cholesterol, low density lipoprotein and high density lipoprotein. Table 1 shows the testing results.

TABLE 1

Lipid-lowering effects in vivo on hyperlipidemia quail of some compounds according to the present invention

| | CHO (mmol/L) | TG (mmol/L) | HDL-C (mmol/L) | LDL-C (mmol/L) | H/L |
|---|---|---|---|---|---|
| 1. Normal Control Group | 4.67 | 0.81 | 2.97 | 1.69 | 2.18 |
| 2. Model Control Group | 12.42 | 0.57 | 4.73 | 8.25 | 0.71 |
| 3. Positive Control Group | 6.51 | 0.76 | 4.39 | 2.51 | 2.19 |
| 4. A14 L | 11.64 | 0.74 | 6.63 | 6.40 | 1.15 |
| 5. A14 H | 7.61 | 0.96 | 4.66 | 3.62 | 1.44 |
| 6. A6 L | 8.65 | 0.70 | 4.89 | 4.61 | 1.21 |
| 7. A6 H | 8.66 | 4.47 | 4.74 | 3.66 | 1.37 |

TABLE 1-continued

Lipid-lowering effects in vivo on hyperlipidemia quail of some compounds according to the present invention

| | CHO (mmol/L) | TG (mmol/L) | HDL-C (mmol/L) | LDL-C (mmol/L) | H/L |
|---|---|---|---|---|---|
| 8. A5 L | 9.66 | 1.95 | 5.35 | 5.07 | 1.29 |
| 9. A5 H | 10.55 | 0.58 | 5.35 | 6.40 | 1.06 |
| 10. A1 L | 8.72 | 0.59 | 5.84 | 3.99 | 1.91 |
| 11. A1 H | 8.05 | 0.51 | 5.31 | 3.63 | 1.54 |
| 12. A10 L | 11.16 | 0.53 | 6.61 | 6.33 | 1.23 |
| 13. A10 H | 7.54 | 1.46 | 4.93 | 2.73 | 2.19 |
| 14. A8 L | 9.11 | 1.50 | 4.75 | 3.46 | 1.58 |
| 15. A8 H | 5.57 | 0.45 | 3.73 | 1.94 | 2.21 |
| 16. A9 L | 9.75 | 1.24 | 4.98 | 5.16 | 1.56 |
| 17. A9 H | 9.18 | 1.26 | 4.98 | 4.08 | 1.54 |
| 18. A11 L | 11.63 | 0.56 | 6.32 | 6.51 | 1.24 |
| 19. A11 H | 8.53 | 0.42 | 5.06 | 4.30 | 1.33 |
| 20. A12 L | 12.40 | 0.54 | 6.21 | 6.75 | 1.43 |
| 21. A12 H | 6.25 | 0.97 | 3.77 | 2.52 | 2.11 |
| 22. A13 L | 14.13 | 0.56 | 6.93 | 9.23 | 0.92 |
| 23. A13 H | 8.88 | 0.35 | 5.64 | 3.95 | 1.79 |

The testing results show an obvious lipid-lowering effect of oral administration of the samples A14, A6, A5, A1, A10, A8, A11, A12, A9, A13. Except for the sample A13 that reduces lipidemia by lowering TG and increasing H/L ratio, the others reduce lipidemia by lowering CHO of hyperlipidemia quail and increasing H/L ratio.

What is claimed is:

1. A quinoline compound represented by formula A, or optical isomer thereof,

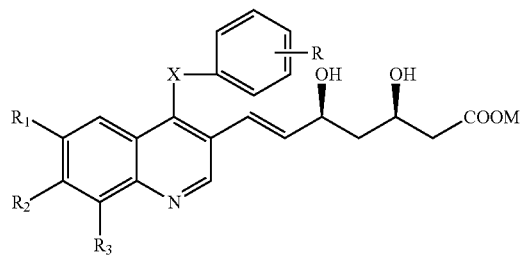

A

Wherein
X is S or O; M is H, Na$^+$, NH$_4^+$ or Ca$^{2+}$; each of R$_1$, R$_2$ and R$_3$ is independently H, halogen, or a substituent represented by formula D or formula E;

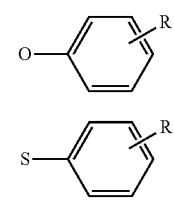

D

E

Wherein
R is H, halogen, C$_1$-C$_4$ alkyl or C$_1$-C$_4$ alkoxy.

2. The quinoline compound, or optical isomer thereof according to claim 1, wherein said halogen is F or Cl.

3. The quinoline compound, or optical isomer thereof according to claim 1, wherein said C$_1$-C$_4$ alkyl is methyl, ethyl, n-propyl, isopropyl, cyclopropyl or n-butyl.

4. The quinoline compound, or optical isomer thereof according to claim 1, wherein said $C_1$-$C_4$ alkoxy is methoxy, ethoxy, n-propoxy, isopropoxy or n-butoxy.

5. The quinoline compound, optical isomer thereof according to claim 1 is selected from the group consisting of:
- (3R,5S)-7-[6,7,8-trifluoro-4-(4-fluorothiophenyl)quinoline-3-yl]-3,5-dihydroxy-6(E)-heptenoic acid sodium salt,
- (3R,5S)-7-[6-fluoro-4,7-di-(thiophenyl)quinoline-3-yl],5-dihydroxy-6(E)-heptenoic acid ammonium salt,
- (3R,5S)-7-[4,6,7,8-tetra-(4-isopropylthiophenyl)quinoline-3-yl],5-dihydroxy-6(E)-heptenoic acid,
- (3R,5S)-7-[6-fluoro-7-chloro-4-(3-methoxythiophenyl)quinoline-3-yl]-3,5-dihydroxy-6(E)-heptenoic acid,
- (3R,5S)-7-[6-fluoro-4,7-di-(3-methoxythiophenyl)quinoline-3-yl]-3,5-dihydroxy-6(E)-heptenoic acid,
- (3R,5S)-7-[6-fluoro-7-chloro-4-(4-fluorophenoxy)quinoline-3-yl]-3,5-dihydroxy-6(E)-heptenoic acid hemi calcium salt,
- (3R,5S)-7-[6-fluoro-7-chloro-4-(3-methoxythiophenyl)quinoline-3-yl]-3,5-dihydroxy-6(E)-heptenoic acid hemi calcium salt,
- (3R,5S)-7-[6-fluoro-4,7-di-thiophenyl)quinoline-3-yl]-3,5-dihydroxy-6(E)-heptenoic acid hemi calcium salt,
- (3R,5S)-7-[6-fluoro-4,7-di-(3-methoxythiophenyl)quinoline-3-yl]-3,5-dihydroxy-6(E)-heptenoic acid hemi calcium salt,
- (3R,5S)-7-[6-fluoro-4,7-di-(4-isopropylthiophenyl)quinoline-3-yl]-3,5-dihydroxy-6(E)-heptenoic acid hemi calcium salt,
- (3R,5S)-7-[6,7,8-trifluoro-4-(4-fluorothiophenyl)quinoline-3-yl]-3,5-dihydroxy-6(E)-heptenoic acid hemi calcium salt,
- (3R,5S)-7-[6,7,8-trifluoro-4-(4-isopropylthiophenyl)quinoline-3-yl]-3,5-dihydroxy-6(E)-heptenoic acid hemi calcium salt,
- (3R,5S)-7-[6,8-difluoro-4,7-di-(phenoxy)-quinoline-3-yl]-3,5-dihydroxy-6(E)-heptenoic acid hemi calcium salt, or
- (3R,5S)-7-[4,6,7,8-tetra-phenoxyquinoline-3-yl]-3,5-dihydroxy-6(E)-heptenoic acid hemi calcium salt.

6. A pharmaceutical composition comprising the treatment effective amount of the quinoline compound, or optical isomer thereof according to claim 1 and a pharmaceutically acceptable carrier.

7. A preparation method of the quinoline compound, or optical isomer thereof according to claim 1, wherein said method is selected from:

Method 1 comprising steps of preparing a compound represented by Formula A by hydrolysis of a compound represented by Formula B under the action of an alkaline in an organic solvent, wherein said alkaline is sodium hydroxide, ammonia-alcohol solution, or calcium hydroxide,

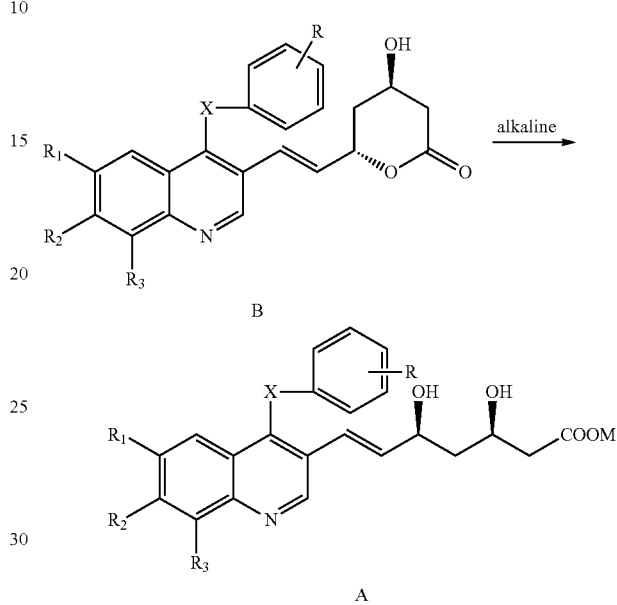

Wherein

M is $Na^+$, $NH_4^+$ or $Ca^{2+}$;

Method 2 comprising steps of preparing a compound represented by Formula A by hydrolysis of a compound represented by Formula B under the action of an alkaline in an organic solvent, adjusting pH value to 7 to 7.5 by addition of an acid and then adding a calcium salt, wherein said alkaline is sodium hydroxide, potassium hydroxide or ammonia-alcohol solution,

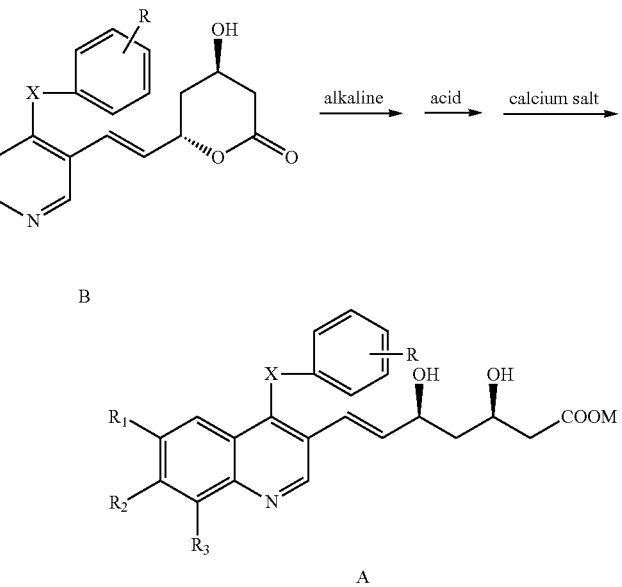

Wherein

M is $Ca^{2+}$;

Method 3 comprising steps of preparing a compound represented by Formula A by hydrolysis of a compound represented by Formula B under the action of an alkaline in an organic solvent and then adjusting pH value to 2 to 3 by addition of an acid, wherein said alkaline is sodium hydroxide, ammonia-alcohol solution, or calcium hydroxide,

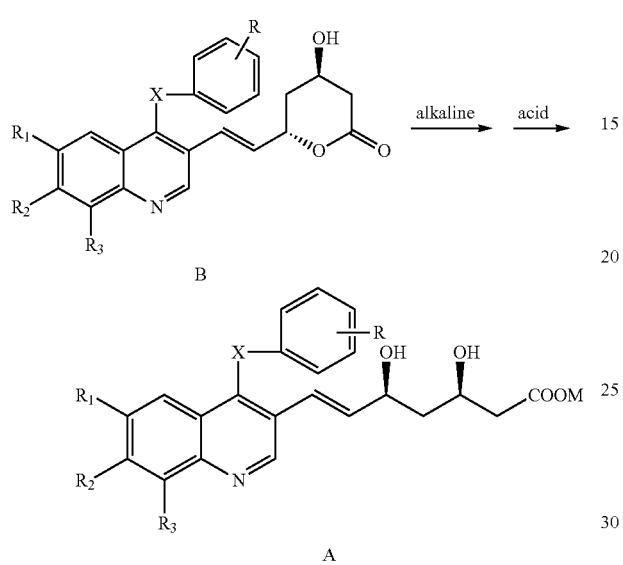

Wherein

M is H;

Method 4 comprising steps of preparing a compound represented by Formula A by reaction of an alkaline and a compound represented by Formula C in an organic solvent, wherein said alkaline is sodium hydroxide, ammonia-alcohol solution, or calcium hydroxide,

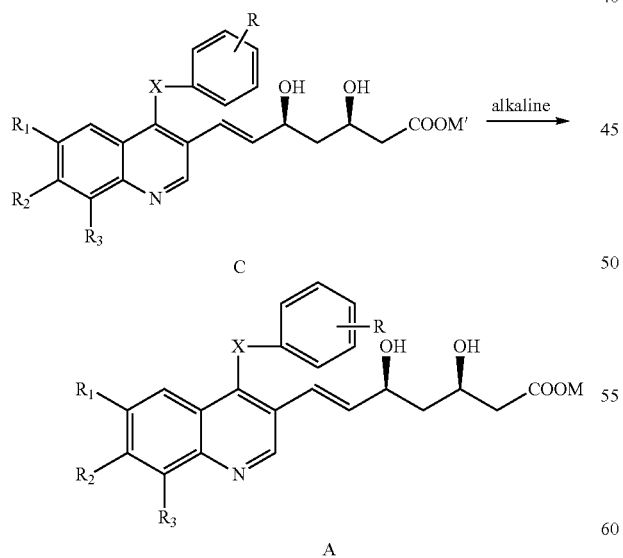

Wherein

M' is H, and M is $Na^+$, $NH_4^+$ or $Ca^{2+}$; and

Method 5 comprising steps of preparing a compound represented by Formula A by reaction of a calcium salt and a compound represented by Formula C in an organic solvent or water,

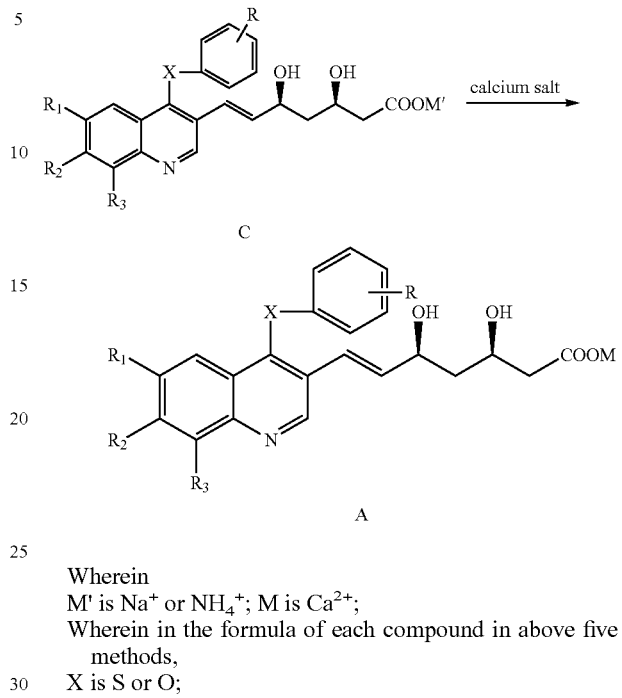

Wherein

M' is $Na^+$ or $NH_4^+$; M is $Ca^{2+}$;

Wherein in the formula of each compound in above five methods,

X is S or O;

each of $R_1$, $R_2$ and $R_3$ is independently H, halogen, or a substituent represented by Formula D or Formula E;

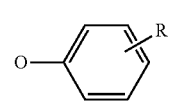

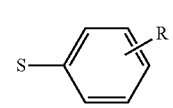

Wherein

R is H, halogen, $C_1$-$C_4$ alkyl or $C_1$-$C_4$ alkoxy.

8. The preparation method according to claim 7, wherein said acid in said method 2 is HCl, $H_2SO_4$, $CH_3COOH$ or $CF_3COOH$; and said calcium salt is $CaCl_2$ or $Ca(CH_3COO)_2$.

9. The preparation method according to claim 7, wherein said acid in said method 3 is HCl, $H_2SO_4$, $CH_3COOH$, or $CF_3COOH$.

10. The preparation method according to claim 7, wherein said calcium salt in said method 5 is $CaCl_2$ or $Ca(CH_3COO)_2$.

11. The preparation method according to claim 7, wherein said organic solvent in each of said five methods is one or more selected respectively from the group consisting of tetrahydrofuran, methyltertbutyl ether, dichloromethane, trichloromethane, toluene, methanol, ethanol, t-butanol, isopropanol, acetone and acetonitrile.

12. The preparation method according to claim 7, wherein the reaction temperature in each of said five methods is respectively 0° C. to 80° C., and the reaction time is respectively 10 min to 8 h.

* * * * *